(12) United States Patent
Schäfer et al.

(10) Patent No.: US 10,172,574 B2
(45) Date of Patent: Jan. 8, 2019

(54) INTERVENTIONAL X-RAY SYSTEM WITH AUTOMATIC ISO-CENTERING

(71) Applicant: KONINKLIJKE PHILIPS N.V., Eindhoven (NL)

(72) Inventors: Dirk Schäfer, Hamburg (DE); Robert Johannes Frederik Homan, Best (NL); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 242 days.

(21) Appl. No.: 15/039,680

(22) PCT Filed: Oct. 27, 2014

(86) PCT No.: PCT/EP2014/072945
§ 371 (c)(1),
(2) Date: May 26, 2016

(87) PCT Pub. No.: WO2015/104075
PCT Pub. Date: Jul. 16, 2015

(65) Prior Publication Data
US 2017/0035374 A1 Feb. 9, 2017

(30) Foreign Application Priority Data
Nov. 27, 2013 (EP) .................................... 13194662

(51) Int. Cl.
*A61B 6/08* (2006.01)
*A61B 6/04* (2006.01)
(Continued)

(52) U.S. Cl.
CPC .................. *A61B 6/08* (2013.01); *A61B 6/02* (2013.01); *A61B 6/04* (2013.01); *A61B 6/0407* (2013.01);
(Continued)

(58) Field of Classification Search
CPC ..... A61B 6/08; A61B 6/481; A61B 2090/365; A61B 2090/371; A61B 2090/373;
(Continued)

(56) References Cited

U.S. PATENT DOCUMENTS 4,558,458 A 12/1985 Katsumata
5,457,724 A 10/1995 Toth
(Continued)

FOREIGN PATENT DOCUMENTS

DE 102011120937 A1 6/2013
WO 2008015612 A2 2/2008

OTHER PUBLICATIONS

Wang, Lejing "Camera Augmented Mobile C-Arm", 2009.

*Primary Examiner* — Chih-Cheng Kao

(57) ABSTRACT

An interventional X-ray system (10), includes a processing unit (30), a table (20) for receiving a patient (44), an X-ray image acquisition device (12) having an X-ray source (16) and an X-ray detector (18) and at least one optical camera (46) adapted for acquiring optical images of a patient (44) situated on the table (20) and for providing image data to the processing unit (30). The processing unit (30) is adapted for segmenting an outline (64) of a patient from an existing three-dimensional model, for receiving acquired images from the at least one camera (46) for determining an optical outline (66) of the patient, for registering the optical outline (66) to the outline (64) obtained in the segmentation and for determining a translation vector (48) representing a required movement of the table for coinciding a center (42) of the anatomy of interest given in the three-dimensional model with the iso-center (38) of a rotational X-ray scan that will be performed. By this process, no X-ray exposure or injection of contrast agent is required.

17 Claims, 3 Drawing Sheets

(51) Int. Cl.
*A61B 6/00* (2006.01)
*A61B 90/00* (2016.01)
*A61B 6/02* (2006.01)
*A61B 5/00* (2006.01)

(52) U.S. Cl.
CPC .......... *A61B 6/0457* (2013.01); *A61B 6/0492* (2013.01); *A61B 6/4417* (2013.01); *A61B 6/4435* (2013.01); *A61B 6/4441* (2013.01); *A61B 6/481* (2013.01); *A61B 6/504* (2013.01); *A61B 6/5247* (2013.01); *A61B 90/361* (2016.02); *A61B 5/0077* (2013.01); *A61B 2090/365* (2016.02); *A61B 2090/371* (2016.02); *A61B 2090/373* (2016.02); *A61B 2090/376* (2016.02)

(58) Field of Classification Search
CPC ... A61B 2090/376; A61B 5/0077; A61B 6/02; A61B 6/04; A61B 6/0407; A61B 6/0457; A61B 6/0492; A61B 6/4417; A61B 6/4435; A61B 6/4441; A61B 6/504; A61B 6/52; A61B 34/20
See application file for complete search history.

(56) References Cited

U.S. PATENT DOCUMENTS

| | | | |
|---|---|---|---|
| 7,446,328 B2 | 11/2008 | Rigney | |
| 8,170,317 B2 | 5/2012 | Movassaghi | |
| 2002/0090058 A1* | 7/2002 | Yasuda | A61B 6/08 378/205 |
| 2005/0089137 A1 | 4/2005 | Toth | |
| 2008/0123937 A1 | 5/2008 | Estrada | |
| 2008/0279331 A1 | 11/2008 | Huang | |
| 2009/0074136 A1 | 3/2009 | Kamegawa | |
| 2009/0262886 A1 | 10/2009 | Mollus | |
| 2009/0285357 A1* | 11/2009 | Khamene | A61B 6/08 378/20 |
| 2011/0002444 A1 | 1/2011 | Schmitt | |
| 2012/0099697 A1* | 4/2012 | Helm | A61B 6/02 378/4 |
| 2012/0302880 A1 | 11/2012 | Tian | |

* cited by examiner

INTERVENTIONAL X-RAY SYSTEM WITH AUTOMATIC ISO-CENTERING

CROSS-REFERENCE TO PRIOR APPLICATIONS

This application is the U.S. National Phase application under 35 U.S.C. § 371 of International Application No. PCT/EP2014/072945, filed on Oct. 27, 2014, which claims the benefit of European Patent Application No. 13194662.6, filed on Nov. 27, 2013. These applications are hereby incorporated by reference herein.

FIELD OF THE INVENTION

The invention relates to an interventional X-ray system, in particular a system using rotational X-ray scans for visualizing a three-dimensional anatomy of a patient, as well as to a method for iso-centering an object of interest to be examined with an interventional X-ray system, an image processing device for iso-centering an object of interest to be examined with an interventional X-ray system, a computer-readable medium and a program element.

BACKGROUND OF THE INVENTION

Rotational X-ray scans are often used for visualizing a patient's three-dimensional anatomy typically by injecting contrast agents to increase an X-ray attenuation of an organ of interest. Due to a limited field of view, X-ray dose and contrast agent dose saving considerations, a proper iso-centering is a crucial part prior to a rotational scan to avoid double scanning.

In the process of iso-centering in particular the patient's underlying table is moved to center a volume of interest on an iso-center of a frame of an X-ray acquisition device. During an acquisition of X-ray images, the frame assumes a particular stationary position except for a circumferential rotation. For example, an X-ray source attached to the frame faces to an X-ray detector at an opposite side of the frame. In operation, as the X-ray beam traverses the inside of the frame, the beam passes through the iso-center. During a circumferential rotation of the frame around its iso-center, the beam rotates around the iso-center, too. Accordingly, the iso-center corresponds to the intersection of the centers of the angular instances of the beam as it rotates.

Current, iso-centering is done manually by injecting small amounts of contrast agent into the organ of interest and by adjusting a table position, with the patient lying on the table, while acquiring several projections from different viewing directions. The success of such an iso-centering process depends on a plurality of conditions, such as the complete filling especially of distal parts of the organ of interest during the iso-centering process and the ability to acquire lateral projections needed for table height positioning, keeping in mind space constraints due to large patients or equipment.

WO 2008/015612 A2 discloses an automated determination of an optimal table position for rotational angiography, which is performed on the basis of determination of a translation vector pointing from a point of gravity of the object of interest to an iso-center of the examination apparatus. Here, multiple two-dimensional projections are conducted.

US 2002/090058 A1 describes an interventional X-ray system including an X-ray tube and an imaging system which detects emitted X-rays and generates X-ray image data. The X-ray tube and the imaging system are supported by a C arm. A three dimensional (3D) workstation is supplied with the generated X ray image data and volume data pertaining to the same specific portion of the same patient as the X-ray image data. From the volume data, 3D image data may be generated. An operator may, through an input device, designate an interest point on the 3D image data, and subsequently the C arm may be moved so that an iso center of the X-ray system is positioned on or near the interest point.

US 2011/0002444 A1 discloses an interventional X ray system with an X ray source and an imaging unit mounted on a C arm. An interface unit receives image data representing an acquired image of an object from the imaging unit. From the image data, position data of object components, for example organs and/or bones of a patient, is determined; the object components positions may then be matched with position data of components of an anatomical model stored in a memory. In particular, the stored anatomical model is adapted so that a virtual projection of the model fits the acquired X ray image. Based on the matching, an image of the adapted anatomical model is generated and presented to a user. Within this image, a component of interest can be selected, following which a carrier of the object is shifted so that the component of interest is positioned to the center of rotation of the X ray system.

SUMMARY OF THE INVENTION

It is desirable to enhance the reliability and preciseness of an iso-centering process, preferably with a reduced X-ray exposition and a reduced contrast agent use.

An interventional X-ray system is proposed, which is able to even eliminate the use of X-rays and contrast agents during the process of iso-centering, while still being extremely precise. Advantageous embodiments and further improvements may be gathered from the sub-claims and the following description.

An interventional X-ray system is proposed, comprising a processing unit, a table for receiving a patient and at least one optical camera adapted for acquiring optical images of a patient situated on the table and for providing image data to the processing unit, wherein the processing unit is adapted for segmenting an outline of a patient from an existing three-dimensional model, receiving acquired images from the at least one camera for determining an optical outline of the patient, registering the optical outline to the outline obtained in the segmentation and determining a translation vector representing a required movement of the table for aligning the anatomy of interest given in the three-dimensional model with the iso-center of a rotational X-ray scan that will be performed.

The proposed interventional X-ray system therefore may comprise any X-ray image acquisition device imaginable for the interventional process itself, as the process of iso-centering does not depend on any X-ray images acquisition at all. For optimally aligning the table in the X-ray image acquisition device, only an existing three-dimensional model needs to be provided, which enables a precise segmentation in order to precisely determine the relationship between the patient's outline and the center of the anatomy of interest.

For example, during a pre-interventional process, at least a part of the patient may undergo an X-ray, CT or MR image acquisition such that a pre-interventional three-dimensional model of the at least one part of the patient's body can be provided to the processing unit. Given the individual characteristics of the patient's body, the center of the anatomy basically is fixed to the outline gained through segmentation. However, also a three-dimensional model from an earlier acquisition may be used, as well as a general model of a human body, which may be adapted to the outline of the patient.

The anatomical model is expected to be a whole body organ model with all relevant organs and the patient outline segmented e.g. from the pre-interventional CT data. A physician may define the center of an "anatomy of interest" based on this segmentation, e.g. the center of gravity of the liver. Missing segmented organs or outlines may be completed by atlas models. Then, the automatic iso-centering is performed.

For being able to adjust or align the table to let the center of the anatomy of interest coincide with the iso-center of the X-ray image acquisition device, the actual optically obtained outline of the patient lying on the table is correlated with the segmented outline from the three-dimensional model. Accordingly, an aspect of the invention may be providing a three-dimensional depth map of the patient lying on the table simply through processing optical images of the patient.

Consequently, neither X-ray exposition nor the use of a contrast agent is required. As the patient lies on the table of the X-ray system, the outline of the patient's body relative to the table is basically fixed and by obtaining optical images from a plurality of different viewing directions an accurate outline of the patient's body is determinable. The optically determined optical outline is registered with the segmented outline from the three-dimensional model. As a result from this process, the position of the three-dimensional model relative to the optical outline is known and, thereby, the position of an anatomy of interest in the three-dimensional model is accurately correlated a position of the table and the C-arm of the X-ray system. Based on this knowledge, a necessary translation vector for moving the center of anatomy of interest to the actual iso-center of the X-ray image acquisition device can easily be calculated.

The optical outline, which may be derived from a three-dimensional optical depth estimation, may be most accurate at the anterior body surface where possible blankets will coincide with the body surface. Together with a known height of the table a good positioning in anterior-posterior direction may be obtained. However, lateral edges may be more difficult due to varying arm positions and/or folded blankets.

The at least one camera may be supported by a fixed or movable gantry, which is supported in a known relationship to the table. For example, a single camera may be used, which is fixedly mounted to a gantry, which is adapted for moving the camera around the table to provide different viewing directions. By providing a plurality of images of the patient's body from different viewing directions under movement of the rotatable gantry, depth information of the patient's body may be acquired.

In case the X-ray image acquisition device is a C-arm system, the gantry may be realized through the C-arm frame itself. Hence, the camera may be moved around the patient by simple moving the C-arm in the desired directions. Also, a separate gantry supporting the single camera may be used.

In an exemplary embodiment, the at least one optical camera comprises a first camera and a second camera, wherein the first camera and the second camera are mounted in fixed positions relative to the table, such that their optical axes are at an angle to each other. With such an arrangement of cameras, different viewing directions are realized through using multiple cameras under elimination of any movement mechanism. For example, at least a stereo view from a region distanced to the table onto a patient lying on the table may be accomplished. Depending on the angle of the optical axes and the distance between the first camera and the second camera, a sufficiently precise depth information may be acquired from the patient's body.

However, it may also be advantageous to use a third camera, a fourth camera and even more cameras to provide a widespread set of images from different viewing directions to achieve result with a maximum precision. Due to continuously decreasing detector sizes for optical cameras and continuously increasing resolutions the cameras may easily be integratable in a distributed fashion on a frame of the X-ray image acquisition device itself.

For a further support, structured light, e.g. in the infrared range, is usable for improving finding corresponding feature points through a plurality of cameras.

In an advantageous embodiment, the optical outline of the patient may be obtained through reconstructing a three-dimensional depth map from the set of images, which comprises an image containing information relating to the distance of the optically visible surface from a viewpoint. This may allow for compensation of an exact alignment of the at least one camera to the patient and, consequently, of the optical outline which is to be registered with the outline from the segmented three-dimensional model.

The three-dimensional model may be based on a set of pre-interventional images, e.g. MRI, CT, PET, SPECT, or through a C-arm imaging system.

However, it may also be feasible to use a general patient model, which is adapted to the outline of the patient. Hence, an initial or pre-interventional scan is not necessary at all.

Further, the processing unit may also be used for automatically iso-center a small region of interest for a second high-resolution scan with a rather tight shuttering. This means that a shutter is used for only selectively letting X-rays pass through to a rather small region of interest. A precise iso-centering is necessary for keeping the X-ray exposure to the patient as little as possible.

The processing unit may still further be adapted for generating an effective center of anatomy for iso-centering purposes, which is a point between a center of anatomy of the organ of interest and e.g. a needle entrance point on the body of the patient, which may be very useful for needle based interventions. For example, the effective center of anatomy may be a point, which has the same distance to the center of anatomy and a further point of interest on the body of the patient.

The interventional X-ray system or the X-ray image acquisition device may comprise a collision detection and avoidance system. This means, that the processing unit is adapted to control the X-ray image acquisition device in such a way that neither the detector, nor the X-ray source, the frame or any other component collides with another component of the interventional X-ray system or the patient. Thus, the processing unit may be adapted for performing the process of iso-centering with respect to the target anatomy while avoiding a collision with the patient, the table or any other objects associated with the interventional X-ray system.

In this regard, supported through this collision avoidance, the distance between the anatomy of interest and the detector may be chosen based on a selected iso-center, but allows avoiding a collision with the patient, while at the same time the distance between the detector and the iso-center may be minimal.

The interventional X-ray system preferably is equipped with a table moving apparatus, which is controllable by the processing unit for moving the table according to the determined movement vector. However, also the X-ray image acquisition device may be moved or both at the same time. As an initial process, not only the motion vector is determined, but the patient and/or the X-ray image acquisition device is automatically moved so as to coincide both centers.

In a preferred embodiment, the processing unit is adapted for coinciding a center of the anatomy of interest given in the three-dimensional model with the iso-center of the rotational X-ray scan that will be performed for aligning the anatomy of interest.

The invention also relates to a method for iso-centering a patient lying on a table to be examined by an interventional X-ray system, as described above. The method comprises providing a model of a patient to a processing unit, acquiring a plurality of optical images from at least one camera of the patient, segmenting the model to determine an outline of the patient model, determining an optical outline of the patient, registering the optical outline to the model outline and determining a movement vector required for aligning the anatomy of interest with the iso-center of the X-ray scan that will be performed. Preferably, aligning comprises coinciding the center of the anatomy of interest with the iso-center.

Further, determining the optical outline of the patient may be realized through obtaining a depth map of the optical images, as explained above.

These and other aspects of the present invention will become apparent from and be elucidated with reference to the embodiments described hereinafter.

DETAILED DESCRIPTION OF EMBODIMENTS

Figure 1:
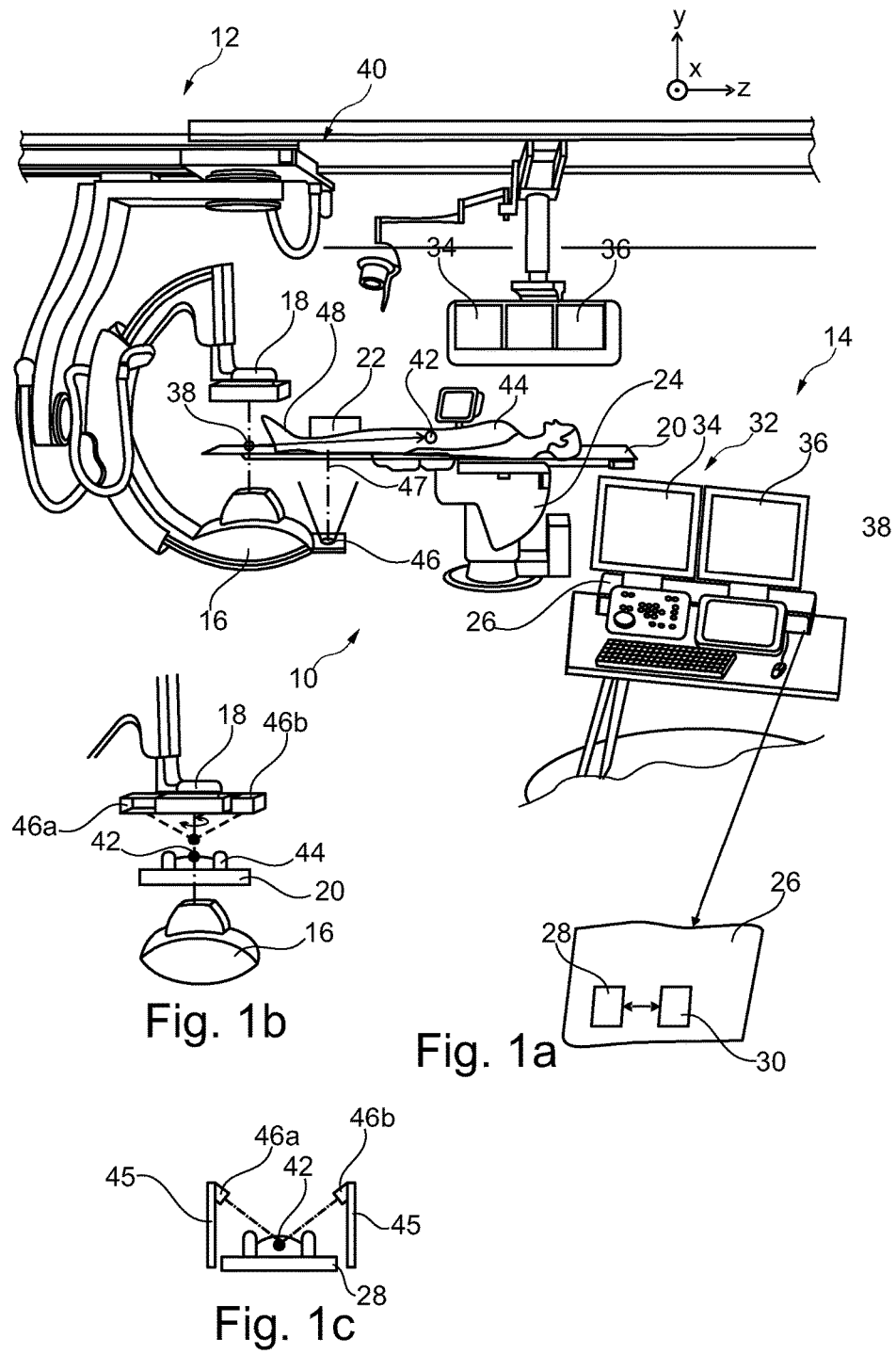
FIGS. 1a, 1b and 1c show an interventional X-ray system in a schematic view.

According to the example of FIG. 1a, an interventional X-ray system 10 is provided, comprising an X-ray image acquisition device 12, and a interventional image viewing device 14. The X-ray image acquisition device 12 comprises an X-ray source 16 and an X-ray detector 18. The X-ray image acquisition device 12 is configured to provide X-ray images of an object. Further, a support table 20, for example for receiving an object, such as a patient, is shown, who may receive a contrast agent from a contrast agent injector 22 for introducing a contrast agent into vessels of a patient during the intervention. A control unit 24 may be present to control the X-ray image acquisition device 12.

It should be noted that the X-ray image acquisition device 12 shown in FIG. 1a is shown as a C-arm structure. However, also other X-ray image acquisition devices, movable or non-movable, may be used without departing from the concept of the invention, as the interventional X-ray system 10 is particularly able to iso-centering a center 42 of an anatomy of a patient 44 on the support table 20 to an iso-center 38 of the X-ray image acquisition device 12, which iso-center position depends on a spatial position of a rail guide 40 in an x-, y- and a z-direction as indicated by a schematically indicated coordinate system in FIG. 1a.

The interventional image viewing device 14 exemplarily comprises a calculation unit 26, which inter alia includes an image data providing unit 28 and a processing unit 30. The interventional image viewing device 14 also comprises a display unit 32 with a first display 34 and a second display 36, which may also be found at the X-ray image acquisition device 12.

The image data providing unit 28 is exemplarily configured to provide interventional images of a region of interest of an object.

The processing unit 30 is adapted for segmenting an outline of the patient 44 from an existing three-dimensional model and for receiving acquired images from at least one camera 46 having a viewing direction 47 for determining an optical outline of the patient 44, wherein the camera 46 is attached to a housing of the X-ray source 16. Due to this arrangement, the viewing direction 47 of the camera 46 may be continuously changed to obtain depth information of the patient 44. However, other exemplary embodiments are possible with one or more cameras fixedly mounted on a steady or movable gantry supported on a ceiling rail.

The processing unit 30 is furthermore adapted for registering the optical outline of the patient 44 to the outline obtained in the segmentation. Resultantly, a translation vector 48 representing a required movement of the support table 20 for coinciding the center 42 of the anatomy of interest given in the three-dimensional model with the iso-center 38 of a rotational X-ray scan that will be performed during the interventional process, preferably under support of a collision avoidance system.

As explained above, the processing unit 30 may also be adapted for generating an effective center of anatomy, in case two positions are of interest at the same time, e.g. a needle entrance point and the organ of interest. Such an effective center of anatomy may be chosen to a position having the same distance to both positions of interest, such as the center of anatomy and the needle entrance point.

A table movement mechanism (not shown in detail) is adapted for moving the support table 20. Together with the rail guide 40, the interventional X-ray system 10 is able to let the iso-center 38 coincide with the center 42 of the anatomy of interest of the patient 44 automatically, after calculating the movement vector 48.

In FIG. 1b, it is indicated that a housing of the detector 18 may carry a first camera 46a and a second camera 46b at opposite ends, wherein the optical axes of both cameras may intersect in a region slightly above the table 20, as indicated with dashed dotted lines.

However, as indicated in FIG. 1c, a fixed gantry 45 may carry the first camera 46a and the second camera 46b independent from the X-ray image acquisition device 12, wherein the optical axes also intersect in a region slightly above the table 20, as indicated with dashed dotted lines.

Figure 2:
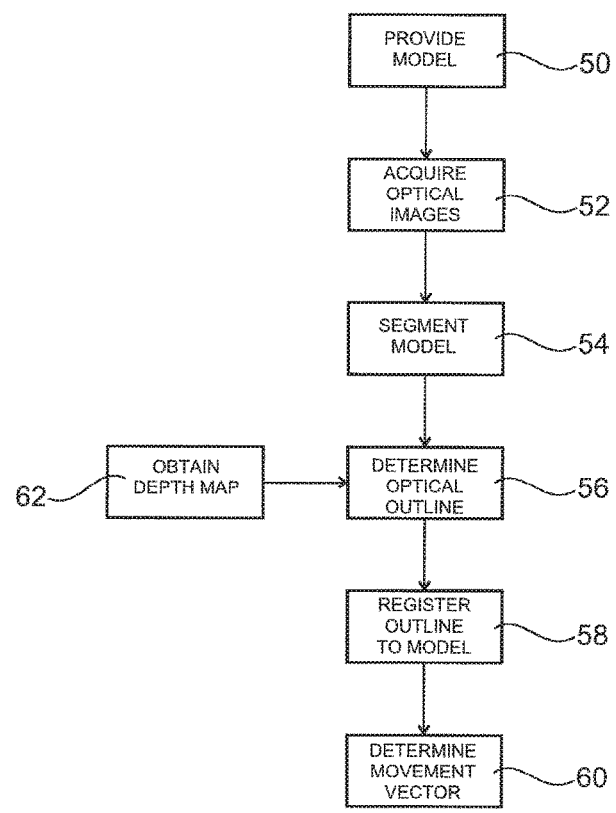
FIG. 2 shows a method for iso-centering an object of interest to be examined with an X-ray system in a schematic view.

In FIG. 2, a schematic, block-oriented method is shown for iso-centering the X-ray image acquisition device 12 in the interventional X-ray imaging system 10. Basically, the method comprises providing 50 a model of a patient to a processing unit 30, acquiring 52 a plurality of optical images from at least one camera 46 of the patient 44, segmenting 54 the model to determine an outline of the patient model, determining 56 an optical outline of the patient, registering 58 the optical outline to the model outline and determining 60 a movement vector required for coinciding the iso-center 38 of the interventional X-ray system and the center 42 of the anatomy of interest.

Further, determining 56 the optical outline of the patient may be realized through obtaining 62 a depth map of the optical images, as explained above.

Figure 3:
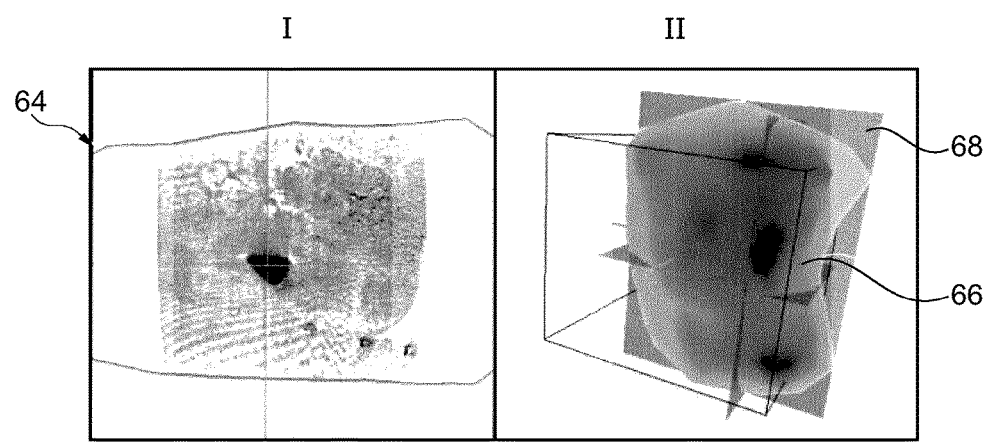
FIG. 3 shows a representation of a three-dimensional model and of a depth map.

Finally, FIG. 3 demonstrates a representation of a three-dimensional model (indicated by I) and a representation of a depth map determined through a set of optical images of the object of interest from a plurality of different viewing directions (indicated by II). An outline 64 of the three-dimensional model may be obtained through a segmentation process. An optical outline 66 may be obtained exemplarily through projection on a certain plane 68. Both outlines 64 and 66 are registered to match their alignments and positions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

10 Interventional X-ray system
12 X-ray image acquisition device
14 Interventional image viewing device
16 X-ray source
18 X-ray detector
20 Support table
22 Contrast agent injector
24 Control unit
26 Calculation unit
28 Image data providing unit
30 Processing unit
32 Display unit
34 First display
36 Second display
38 Iso-center
40 Rail guide
42 Center of anatomy of interest
44 Patient
45 Gantry
46, 46a, 46b Camera
47 Viewing direction
48 Translation vector
50 Providing a model
52 Acquiring optical images
54 Segmenting model
56 Determining optical outline
58 Registering optical outline to model outline
60 Determining movement vector
62 Obtaining depth map
64 Outline
66 Optical outline
68 Plane

The invention claimed is:

1. An interventional X-ray system, comprising:
a processing unit,
a table for receiving a patient,
an X-ray image acquisition device having an X-ray source and an X-ray detector and
at least one optical camera adapted for acquiring optical images of the patient received on the table and for providing optical image data to the processing unit, wherein the processing unit is adapted for segmenting an outline of a patient from a three-dimensional model, receiving acquired images from the at least one optical camera for determining an optical outline of the patient, registering the optical outline to the outline obtained in the segmentation and determining a translation vector representing a required movement of the table for aligning an anatomy of interest in the three-dimensional model with an iso-center of a rotational X-ray scan that will be performed.

2. The interventional X-ray system of claim 1, wherein the at least one camera is mounted to a gantry, which is adapted for moving the camera around the table to provide different viewing directions.

3. The interventional X-ray system of claim 1, wherein the X-ray image acquisition device is a C-arm system and wherein the at least one camera is mounted to a frame of the X-ray image acquisition device.

4. The interventional X-ray system of claim 1, wherein the at least one optical camera comprises a first camera and a second camera, wherein the first camera and the second camera are mounted on a gantry with fixed positions relative to the table, such that their optical axes are at an angle to each other.

5. The interventional X-ray system of claim 1, wherein obtaining the optical outline of the patient is conducted through reconstructing a three-dimensional depth map from the set of optical images.

6. The interventional X-ray system of claim 5, wherein the three-dimensional model is based on a set of pre-interventional images.

7. The interventional X-ray system of claim 5, wherein the three-dimensional model is a general patient model, which is adapted to the optical outline of the patient.

8. The interventional X-ray system of claim 7, wherein the processing unit is adapted for generating an effective center of anatomy, which is a point between a center of anatomy of an organ of interest and a needle entrance point on the body of the patient.

9. The interventional X-ray system of claim 1, further comprising a collision avoidance system, wherein the processing unit is adapted for minimizing the distance between the iso-center and the X-ray detector under avoiding a collision with the patient on the table.

10. The interventional X-ray system of claim 9, wherein the processing unit is adapted for coinciding a center of the anatomy of interest given in the three-dimensional model with the iso-center of the rotational X-ray scan that will be performed for aligning the anatomy of interest.

11. Method for iso-centering a patient lying on a table to be examined by an interventional X-ray system, comprising:

providing a three dimensional model of a patient to a processing unit, acquiring a plurality of optical images from at least one camera of the patient, segmenting the model to determine a segmented outline of the patient, determining, from the optical images, an optical outline of the patient, registering the optical outline to the segmented outline and determining a movement vector required for aligning an anatomy of interest in the three dimensional model with an iso-center for a rotational X-ray scan to be performed.

12. Method according to claim 11, further comprising obtaining a depth map of the optical images for obtaining the optical outline of the patient.

13. A non-transitory computer-readable medium, in which a computer program for iso-centering an object of interest to be examined with an interventional X-ray system is stored which, when being executed by a processing unit, causes the processing unit to carry out the method of claim 11.

14. A processing unit for iso-centering an object of interest to be examined with an X-ray image acquisition device, the processing unit comprising:

a memory for storing a three-dimensional model of the object of interest, wherein the processing unit is adapted for segmenting an outline of a patient from the three-dimensional model and for determining an optical outline of the patient from a plurality of optical images acquired from different viewing angles, and wherein the processing unit is adapted for registering the optical outline to the outline obtained in the segmentation and for determining a translation vector representing a required movement for coinciding a center of an anatomy of interest given in the three-dimensional model with an iso-center of a rotational X-ray scan that will be performed.

15. An interventional X-ray system, comprising:

an X-ray source and an X-ray detector mounted to a gantry configured to rotate the X-ray source and detector around an iso-center;

a table configured to support a patient with anatomy of interest at the iso-center;

at least one optical camera configured to generate optical image data of the patient supported on the table;

one or more processors configured to:

segment a patient model outline from a three-dimensional model, receive the optical image data from the at least one optical camera, determine an optical outline of the patient from the optical image data, register the optical outline to the patient model outline, determine a translation vector representing movement between the table and the gantry which aligns the anatomy of interest in the three-dimensional model with the iso-center, and control at least one of the gantry and the table in accordance with the translation vector.

16. The interventional X-ray system of claim 15, wherein the gantry includes a C-arm.

17. The interventional X-ray system of claim 15, wherein the one or more processors are further configured to:

after controlling one of the gantry and the table in accordance with the translation vector, activate the X-ray source and the X-ray detector to generate diagnostic image data;

reconstruct the diagnostic image data into a diagnostic image; and control a display device to display the diagnostic image.

* * * * *